United States Patent
Ishii et al.

(10) Patent No.: US 9,517,192 B2
(45) Date of Patent: Dec. 13, 2016

(54) BODY COSMETICS FOR WETTED SKIN

(71) Applicant: KAO CORPORATION, Tokyo (JP)

(72) Inventors: Tomomi Ishii, Sumida-ku (JP);
Takaaki Hori, Sumida-ku (JP);
Kazuhiro Yamaki, Sumida-ku (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 14/556,687

(22) Filed: Dec. 1, 2014

(65) Prior Publication Data

US 2015/0086502 A1 Mar. 26, 2015

Related U.S. Application Data

(62) Division of application No. 12/672,287, filed as application No. PCT/JP2008/002027 on Jul. 30, 2008, now Pat. No. 8,933,125.

(30) Foreign Application Priority Data

Aug. 9, 2007 (JP) ................. 2007-207684

(51) Int. Cl.
| | | |
|---|---|---|
| *A61K 8/81* | (2006.01) | |
| *A61K 8/31* | (2006.01) | |
| *A61Q 19/00* | (2006.01) | |
| *A61K 8/34* | (2006.01) | |
| *A61K 8/37* | (2006.01) | |
| *A61K 8/06* | (2006.01) | |
| *A61K 8/36* | (2006.01) | |

(52) U.S. Cl.
CPC ............... *A61K 8/8147* (2013.01); *A61K 8/06* (2013.01); *A61K 8/062* (2013.01); *A61K 8/31* (2013.01); *A61K 8/342* (2013.01); *A61K 8/345* (2013.01); *A61K 8/36* (2013.01); *A61K 8/361* (2013.01); *A61K 8/37* (2013.01); *A61Q 19/00* (2013.01); *A61Q 19/007* (2013.01); *A61K 2800/10* (2013.01)

(58) Field of Classification Search
CPC ............ A61K 8/06; A61K 8/062; A61K 8/31; A61K 8/345; A61K 8/36; A61K 8/342; A61K 8/361; A61K 8/37; A61K 8/8147; A61K 2800/10; A61Q 19/00; A61Q 19/007
See application file for complete search history.

(56) References Cited

U.S. PATENT DOCUMENTS

| | | | |
|---|---|---|---|
| 3,664,734 A | 5/1972 | Rivoire et al. | |
| 5,827,920 A | 10/1998 | Watanabe et al. | |
| 5,925,364 A | 7/1999 | Ribier et al. | |
| 6,074,652 A | 6/2000 | Ishiwatari et al. | |
| 6,699,488 B2 | 3/2004 | Deckner et al. | |
| 8,080,239 B2 | 12/2011 | Matsuo et al. | |
| 2005/0250658 A1 | 11/2005 | Putman et al. | |
| 2006/0182870 A1 | 8/2006 | Nakamura et al. | |

FOREIGN PATENT DOCUMENTS

| | | |
|---|---|---|
| EP | 1 390 006 | 2/2004 |
| JP | 2-202809 | 8/1990 |
| JP | 8-127526 | 5/1996 |
| JP | 10-95706 | 4/1998 |
| JP | 10-291924 | 4/1998 |
| JP | 11-279021 | 10/1999 |
| JP | 2001-302457 | 10/2001 |
| JP | 2001-354510 | 12/2001 |
| JP | 2004-51505 | 2/2004 |
| JP | 2004-231518 | 8/2004 |
| JP | 2005-139094 A | 6/2005 |
| JP | 2005-526118 | 9/2005 |
| JP | 2006-290762 | 10/2006 |
| JP | 2007-314442 | 12/2007 |
| JP | 2008-74779 | 4/2008 |
| TW | 522018 B | 3/2003 |
| WO | 97/44001 | 11/1997 |
| WO | 98/07404 | 2/1998 |
| WO | WO 03/094867 A1 | 11/2003 |

OTHER PUBLICATIONS

Extended Search Report issued Feb. 12, 2015 in European Patent Application No. 08790291.2.
Masami, JP 2001-302455, published: Oct. 31, 2001, Machine English Translation.
Japanese Office Action issued Feb. 12, 2013, in Patent Application No. 2007-207684 (with English translation).
Inchem (Petrolatum MSDS; validated: Mar. 6, 2002).
Sigma Aldrich, Beeswax MSDS (Revision Date Jul. 19, 2010).
Office Action issued Jul. 26, 2011 in Chinese Patent Application No. 2000880102687.2 (with English translation).
Neimeier, R.W., Petroleum, Coal Tar and Related Products, Patty's Toxicology, $5^{th}$ Ed. (2001).

*Primary Examiner* — Ali Soroush
*Assistant Examiner* — Genevieve S Alley
(74) *Attorney, Agent, or Firm* — Oblon, McClelland, Maier & Neustadt, L.L.P.

(57) ABSTRACT

A body cosmetic for application to wetted skin after bathing, and the like, which provide high moisturizing effects, spread well to all over the body, and are easy to apply.
An oil-in-water body cosmetic for application to wetted skin, which contains a water-soluble polymer and the following components (A) to (C):
(A) from 20 to 50% by mass of oily ingredients containing (A1) oil that is pasty at 25° C. and (A2) polar oil that is liquid at 25° C.;
(B) from 11 to 50% by mass of glycerin; and
(C) from 20 to 60% by mass of water;
in this body cosmetic for application to wetted skin, the content of the pasty oil (A1) is from 1 to 20% by mass, and the content of the liquid polar oil (A2) is from 1 to 20% by mass

16 Claims, 1 Drawing Sheet

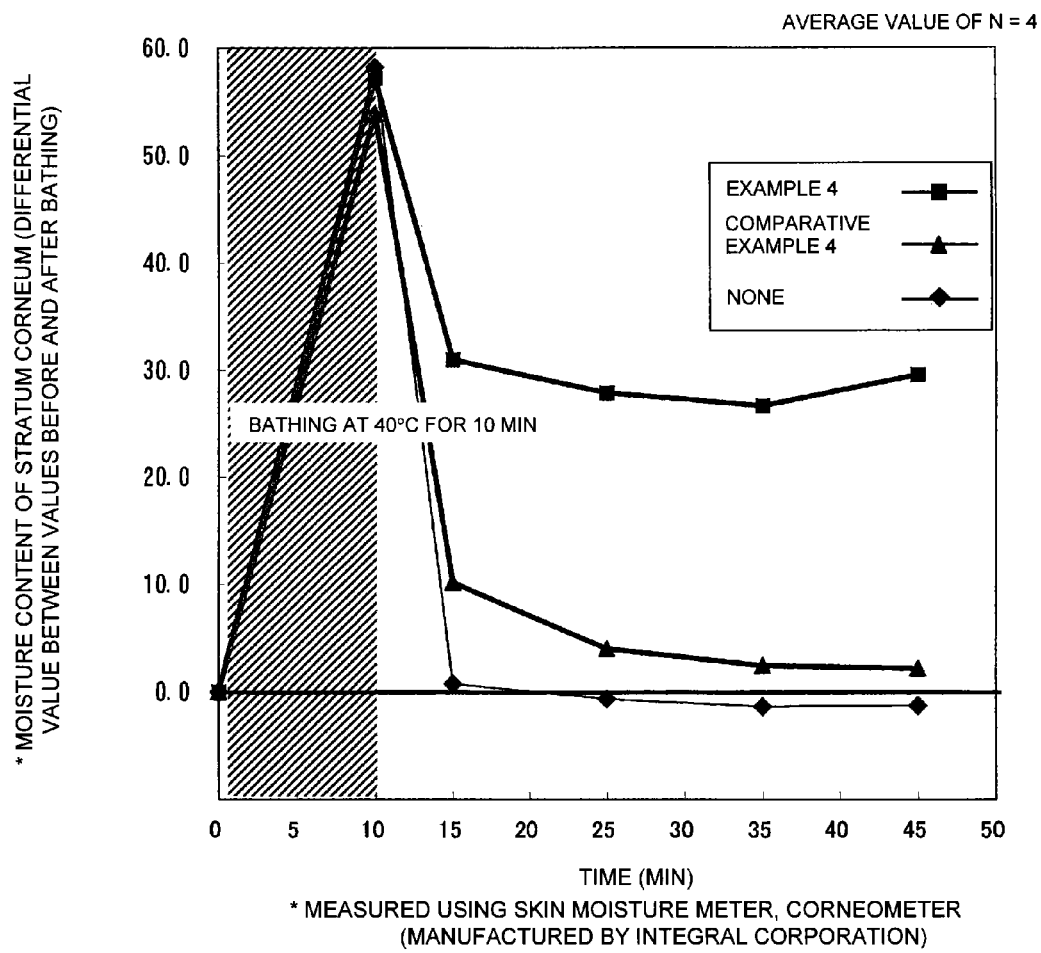

BODY COSMETICS FOR WETTED SKIN

This application is a divisional of U.S. application Ser. No. 12/672,287 filed Feb. 5, 2010, which is a National Stage of PCT/JP2008/002027 filed Jul. 30, 2008, both of which are incorporated herein by reference. This application also claims the benefit of JP 2007-207684 filed Aug. 9, 2007.

FIELD OF THE INVENTION

The present invention relates to body cosmetics for application to wetted skin, and a skin care method using the same.

BACKGROUND OF THE INVENTION

Conventionally, a variety of skin care cosmetics intended for the face, hands, and the like have been widely used to prevent skin dryness or roughness. In recent years, however, skin care cosmetics for the whole body have been used, because skin dryness or roughness occurs not only on faces but also on extensive parts of a body such as hands, arms and legs. Such skin care cosmetics are required to have non-stickiness and ease of application to the whole body, in addition to excellent moisturizing effects. Usually, as skin care agents or skin conditioners for use after bathing or for use in a daily routine, body lotions or milks on dry skin and the like are used. And for use in a bathing, shower agents and the like are also used. From this point of view, body rinse compositions used by applying to wetted skin after bathing and lightly rinsing off (JP-A-02-202809), rinsable skin conditioning compositions (JP-A-2005-526118), shower agents (JP-A-2004-231518), and the like have been developed.

SUMMARY OF THE INVENTION

The present invention provides an oil-in-water body cosmetic for application to wetted skin, which contains a water-soluble polymer and the following components (A) to (C):

(A) from 20 to 50% by mass of oily ingredients containing (A1) oil which is pasty at 25° C. and (A2) polar oil which is liquid at 25° C.;
(B) from 11 to 50% by mass of glycerin; and
(C) from 20 to 60% by mass of water;

The content of the pasty oil (A1) in the cosmetic is from 1 to 20% by mass, and the content of the liquid polar oil (A2) in the cosmetic is from 1 to 20% by mass.

BRIEF DESCRIPTION OF THE DRAWING

FIG. 1 is a diagram illustrating a change with time in a moisture content of a stratum corneum when samples are applied to wetted skin after bathing.

DETAILED DESCRIPTION OF THE INVENTION

The above-described conventional cosmetics for the whole body are used by applying to wetted skin and then rinsing off in a shower or the like, and hence were difficult to provide sufficient skin care benefits because of low retention of moisturizers, i.e., active ingredients. Moreover, increasing the retention of moisturizers problematically caused a sticky feeling, and caused spreading on skin to deteriorate, making the application unpleasant.

In contrast, the present invention provides body cosmetics for application to wetted skin after bathing or the like, having high moisturizing effects, well spread to all over the body, and easy application.

Thus, the present inventors paid attention to an oil-in-water emulsion containing a water-soluble polymer. And they added a certain amount of pasty oil and liquid oil in combination into the emulsion as oily ingredients, and further added a large amount of glycerin thereto. As a result, the emulsion spreads extremely well when applied to wetted skin, and provides enhanced and long-lasting moisturizing effects. Moreover, the inventors found that the oil-in-water cosmetics of the invention need not be rinsed off after application to wetted skin, and when dried by a towel, the cosmetics can provide excellent skin care benefits.

The body cosmetics of the present invention spread extremely well when applied directly to wetted skin, and provide good moisturizing effects after application, such as a moist feeling, and a smooth feeling, which last for a long time. In addition, the body cosmetics can show the above-described excellent effects simply by applying to wetted skin and then towel drying; hence, they can provide these effects only by a simple process after bathing, and can also provide light feeling; therefore, they exhibit excellent effects.

The body cosmetics for wetted skin of the present invention are in the form of oil-in-water emulsions wherein oily ingredients are dispersed in an aqueous phase containing a water-soluble polymer. It is considered that is the reason why the body cosmetics of the invention can spread well when applied to wetted skin, and also allow each of the oily ingredients and glycerin to adsorb on the skin surface and further form a membrane onto it, thereby retaining excellent moisturizing effects for a long time.

Examples of water-soluble polymers for use in the body cosmetics of the invention include natural polymers such as plant polysaccharides, microorganism polysaccharides, and animal proteins; semi-synthetic polymers such as celluloses, starches, alginates, and polysaccharide derivatives; synthetic polymers such as vinyl polymers.

Examples of plant polysaccharides include guar gum, roast bean gum, quince seed gum, gum arabic, tragacanth gum, carrageenan, galactan, pectin, mannan, and starches.

Examples of microorganism polysaccharides include xanthan gum, dextran, pullulan, succinoglucan, curdlan, and hyaluronic acid.

Examples of animal proteins include gelatin, casein, albumin, collagen, and keratin.

Examples of celluloses include methylcellulose, ethylcellulose, hydroxyethylcellulose, hydroxypropylcellulose, carboxymethylcellulose, and hydroxypropylmethylcellulose.

Examples of starches include soluble starches, carboxymethyl starch, and methyl starch.

Examples of alginates include propylene glycol alginate, and sodium alginate.

Examples of polysaccharide derivatives include derivatives having polysaccharide backbones other than celluloses, starches, and alginates, such as dextran sulfate, and carboxymethyl chitin.

Examples of synthetic polymers include vinyl polymers such as polyvinyl alcohol, polyvinyl pyrrolidone, polyvinyl methyl ether, carboxyvinyl polymers, alkyl-modified carboxyvinyl polymers (acrylate-alkyl methacrylate copolymer, etc.), and sodium polyacrylate, as well as polyethylene glycol, and ethyleneoxide-propyleneoxide block copolymer. Commercially available products are usable as these synthetic polymers, and examples of alkyl acrylate copolymers include Aculyn 33 (ISP Corp.); examples of acrylate-alkyl methacrylate copolymers include Pemulen TR-1, Pemulen TR-2, Carbopol 1382, and Carbopol ETD 2020 (all from Noveon INC.) and Aqupec HV-501ER (Sumitomo Seika Chemicals, Co., Ltd.); and examples of (meth)acrylate acid-alkyl (meth)acrylate copolymer derivatives or salts thereof include alkyl acrylate-alkyl methacrylate-polyoxyethylene (20)stearylether copolymer (Aculyn 22) (ISP Corp.).

Among these water-soluble polymers, quince seed gum, tragacanth gum, pectin, xanthan gum, gelatin, casein, methylcellulose, hydroxyethylcellulose, hydroxypropylcellulose, carboxymethylcellulose, hydroxypropylmethylcellulose, sodium alginate, carboxyvinyl polymers, alkyl-modified carboxyvinyl polymers, sodium polyacrylate, and the like are preferred. Alkyl-modified carboxyvinyl polymers, carboxyvinyl polymers, and carboxymethylcellulose are more preferable to provide stability and dispersibility during dilution to the oil-in-water emulsions.

A content of the water-soluble polymer in the body cosmetics of the invention is preferably from 0.01 to 10% by mass (hereinafter simply denoted as %), and more preferably from 0.05 to 5%, to provide stability, ease of application, and moisturizing effects to the oil-in-water emulsions.

The body cosmetics of the invention are in the form of oil-in-water emulsions wherein oily ingredients are dispersed in an aqueous phase containing any of the above-mentioned water-soluble polymers. Examples of oily ingredients (A) include those typically used in cosmetics to improve the moisturizing properties, the touch feeling, and the like, such as fats and oils, waxes, hydrocarbons, silicone oils, esters, higher fatty acids, higher alcohols, and cyclic alcohols. These oily ingredients (A) are contained in the body cosmetics of the invention in an amount of from 20 to 50%, preferably from 20 to 40%, and more preferably from 25 to 35%, to provide moisturizing effects and reduce sticky feeling. The oily ingredients (A) contain (A1) oil which is pasty at 25° C. and (A2) polar oil which is liquid at 25° C.

In the body cosmetics of the invention, it should contain these oily ingredients, including from 1 to 20% of (A1) the oil which is pasty at 25° C., and from 1 to 20% of (A2) the polar oil which is liquid at 25° C. Examples of the oils which are pasty at 25° C. include oily ingredients having melting points of 30 to 90° C., and preferably 35 to 80° C.; detailed examples thereof include hydrocarbon oils, and ester oils. Among these examples, hydrocarbon oils are more preferable to provide moisturizing effects derived from their occlusive properties. Examples of hydrocarbon oils include vaseline, paraffin, ozokerite, ceresin, and microcrystalline wax. Among these examples, vaseline and paraffin are still more preferable.

These pasty oils (A1) are preferably contained in the cosmetics of the invention in an amount of from 1 to 10%, and more preferably from 2 to 8%, to provide moisturizing effects derived from their occlusive properties.

Examples of the polar oils (A2) which are liquid at 25° C. include esters, higher fatty acids, and higher alcohols. Examples of esters include esters of higher fatty acids with 8 or more carbon atoms and alcohols, such as oleyl oleate, decyl oleate, propyleneglycol dioleate, hexyldecyl dimethyloctanate, butyl stearate, isopropyl palmitate, diethyl phthalate, isopropyl myristate, octyldodecyl myristate, myristyl myristate, ethylene glycol monostearate, propylene glycol monostearate, hexyl laurate, cetyl 2-ethylhexanoate, and cholesteryl ester. Examples of higher fatty acids include higher fatty acids with 12 to 28 carbon atoms, such as isostearic acid, oleic acid, linolenic acid, and linoleic acid. Examples of higher alcohols include higher alcohols with 12 to 28 carbon atoms, such as oleyl alcohol.

These liquid polar oils (A2) are preferably contained in the cosmetics of the invention in an amount of from 3 to 18%, and more preferably from 5 to 15%, to provide a spreading effect on wetted skin.

In the present invention, it is important that the pasty oil (A1) and the liquid polar oil (A2) should be contained in the oily ingredients (A) in above mentioned range, to achieve both excellent moisturizing effects and a spreading effect of the oily ingredients on wetted skin. In order to achieve these effects, the mass ratio of the ingredient (A1) to the ingredient (A2) is preferably from 1:20 to 10:1, more preferably from 1:20 to 5:1, and still more preferably from 1:10 to 2:1.

In addition to the ingredients (A1) and (A2), the oily ingredients (A) may contain fats and oils, waxes, silicone oils, cyclic alcohols, and the like. Examples of fats and oils include avocado oil, linseed oil, almond oil, hoof oil, olive oil, liver oil, apricot kernel oil, sesame oil, wheat germ oil, rice bran oil, rice germ oil, camellia sasanqua oil, safflower oil, cinnamon oil, soybean oil, tea seed oil, evening primrose oil, camellia oil, corn oil, rapeseed oil, persic oil, castor oil, sunflower oil, grape oil, jojoba oil, macadamia nut oil, mink oil, cotton seed oil, arachis oil, and yolk oil. Examples of waxes include yellow beeswax, carnauba wax, spermaceti wax, lanolin, liquid lanolin, reduced lanolin, hard lanolin, candelilla wax, cotton wax, bayberry wax, Chinese wax, montan wax, bran wax, kapok wax, sugarcane wax, jojoba wax, wool wax, and shellac wax. Examples of silicone oils include dimethylpolysiloxane, methylcyclopolysiloxane, diethylpolysiloxane, methylphenyl polysiloxane, amino-modified polysiloxane, fluorine-modified polysiloxane, alkyl-modified polysiloxane, alcohol-modified polysiloxane, and fatty acid-modified polysiloxane. Examples of cyclic alcohols include menthol. The content of these oily ingredients other than the ingredients (A1) and (A2) in the cosmetics of the invention is preferably from 1 to 30%, more preferably from 5 to 25%, and still more preferably from 10 to 20%, to improve the touch feeling.

It is important that the body cosmetics of the invention contain from 11 to 50% of (B) glycerin, to provide a moist feeling on skin after application to wetted skin, and excellent moisturizing effects. The content of glycerin is more preferably from 15 to 45%, and still more preferably from 15 to 35%. Since a large amount of glycerin is contained therein, the body cosmetics of the invention provide notably excellent moisturizing effects when applied to skin and then dried by a towel.

Since the body cosmetics of the invention are used by directly applying to wetted skin, they preferably contain the oily ingredients (A) and glycerin (B) in a total amount of 80% or less, and more preferably from 30 to 70%, to provide wet spreadability and non-stickiness at the time of application to wetted skin, as well as a moist feeling and non-stickiness after towel drying.

The body cosmetics of the invention contain water (C) in an amount of from 18 to 60%, preferably from 20 to 60%, more preferably 25 to 55%, and still more preferably from 30 to 50%, from a viewpoint of stability.

The body cosmetics of the invention may further contain an alcohol as a solvent or an anti-freezing agent. Examples of preferable alcohols include lower alcohols with 1 to 5 carbon atoms and polyhydric alcohols with 2 to 6 carbon atoms, such as ethyl alcohol, propylene glycol, 1,3-butylene glycol, dipropylene glycol, and sorbitol.

In addition to the above-described ingredients, the body cosmetics of the invention may contain various medicinal components, anti-inflammatory agents, skin lightening agents, UV blocking agents, antimicrobial agents, antiperspirants, preservatives, antioxidants, pigments, perfumes, and the like. Insofar as the effects of the invention are not impaired, the body cosmetics may further contain a small amount of surfactants, preferably in an amount of 1% or less, more preferably 0.5% or less, and still more preferably 0.1% or less.

Various medicinal components can include such as blood circulation promoters such as methyl nicotinate, ethyl nicotinate, benzyl nicotinate, tocopherol nicotinate, and like nicotinic acid derivatives, nonylic acid vanillylamide, methyl linoleate, ethyl linoleate, and like linoleic acid derivatives, octylphthalide and like phthalide derivatives, and γ-orizanol; and cooling agents such as l-menthol, peppermint oil, and camphor.

Examples of anti-inflammatory agents include salts of glycyrrhizic acid, β-glycyrrhetic acid, allantoin, indomethacin, guaiazulene, guaiazulene sulfonate, crude drug extracts, and herb extracts.

Examples of skin lightening agents and UV blocking agents include vitamin C derivatives (such as magnesium ascorbyl phosphate), arbutin, kojic acid, chamomile extracts, Parsol MCX, Escarol 507, oxybenzone, and Uvinul.

Examples of antimicrobial agents include benzalkonium chloride, benzethonium chloride, chlorhexidine, trichlorocarbanilide, cetylpyridinium chloride, and isopropylmethyl phenol.

Examples of antiperspirants include ammonium chloride, chlorohydroxyaluminum, aluminum lactate, allantoin aluminum derivative, and zinc p-phenolsulfonate.

The body cosmetics of the invention preferably further contain a water-insoluble powder to improve the skin feeling upon application, such as a silky feeling, and a smooth feeling.

Examples of water-insoluble powders include inorganic powders such as talc, sericite, mica, kaolin, red oxide, clay, silicic acid, silicic acid anhydride, magnesium silicate, mica isinglass, magnesium oxide, zinc oxide, titanium oxide, aluminum oxide, aluminum sulfate, alum, calcium sulfate, barium sulfate, and magnesium sulfate; organic powders such as polyamide, polyester, polyethylene, polypropylene, polystyrene, ethylene-acrylic acid polymer, styrene-acrylic acid copolymer, polyurethane, vinyl resin, polycarbonate resin, nylon, silk, cellulose powder, silicone powder, and polyacrylic acid. Among these examples, talc, sericite, mica, kaolin, and silicone powder are preferable in the body cosmetics of the invention because they can provide a good feeling on skin.

These powder particles may have any of flat, mass, scaly, spherical and like shapes. Among them, particles with flat, scaly, spherical, and like shapes are preferable to improve the skin feeling.

These water-insoluble powders preferably have a mean particle size of from 0.1 to 15 μm, and more preferably from 1 to 10 μm, as determined by a laser diffraction/scattering method, to prevent a rough feeling on the skin, and provide a silky feeling to improve the feeling at the time of application.

The content of these water-insoluble powders in the body cosmetics of the invention is preferably from 0.5 to 60%, and more preferably from 1 to 25%, to improve the feeling at the time of application.

Since the body cosmetics of the invention are in a form of oil-in-water emulsions wherein oily ingredients are dispersed in an aqueous phase containing a water-soluble polymer, these emulsions can be stably blended with a large amount of glycerin, and can also provide the effects of the invention, as described above. In order to produce such stable emulsions, the oily phase/aqueous phase mass ratio is preferably from 10/90 to 50/50, more preferably from 15/85 to 45/55, and still more preferably from 20/80 to 40/60.

The body cosmetics of the invention preferably have a viscosity of from 1,000 to 100,000 mPa.s, and more preferably from 3,000 to 30,000 mPa.s, to achieve stability of the oil-in-water emulsions. The measurement conditions are as follows: equipment used: a BM-type viscometer (manufactured by Tokyo Juki Co., Ltd.); rotor: No. 4; rotation speed: 12 r/min; measurement time: 60 sec; measurement temperature: 25° C.

The body cosmetics of the invention are used by applying to wetted skin after bathing, showering, or the like. When applied to wetted skin, the body cosmetics spread well to the skin, and release the oil-in-water emulsions, which then are attached to the skin surface. At that time, the pasty oil, the liquid polar oil and glycerin are also uniformly attached all over the skin, such that the three ingredients synergistically provide high moisturizing effects and a smooth feeling which last for a long time. After application, the body cosmetics of the invention may be rinsed off in a shower, however, it is more preferred that they are dried with a towel to be left on the skin.

EXAMPLES

Examples 1 to 8 and Comparative Examples 1 to 5

The ingredients listed in Table 1 were uniformly mixed to prepare emulsions. A forearm washed with a soap was soaked in hot water at 40° C. for 10 minutes, and then 0.4 g of each sample composition was spread by hand all over the wetted forearm, and the forearm was wiped with a towel. The ease of application during spreading and the moist feeling and non-stickiness on the forearm after wiping with a towel were evaluated.

[Evaluation Criteria for Ease of Application]

The ease of application of each sample to wetted forearm was rated according to a following criteria: 5: very easy to spread; 4: easy to spread; 3: rather easy to spread; 2: rather hard to spread; 1: hard to spread, using an average value of ratings of three expert panelists.

[Evaluation Criteria for Moist Feeling]

The moist feeling on the forearm after being wiped with a towel was rated according to a following criteria: 5: very moist; 4: moist; 3: rather moist; 2: not very moist; 1: not moist, using an average value of ratings of three expert panelists.

[Evaluation Criteria for Non-Stickiness]

The non-stickiness on the forearm after being wiped with a towel was rated according to a following criteria: 5: not sticky; 4: not very sticky; 3: rather sticky; 2: sticky; 1: very sticky, using an average value of ratings of three expert panelists.

The results are shown in Table 1.

TABLE 1

|   |   | Examples | | | | | | | | Comparative Examples | | | | |
|---|---|---|---|---|---|---|---|---|---|---|---|---|---|---|
|   |   | 1 | 2 | 3 | 4 | 5 | 6 | 7 | 8 | 1 | 2 | 3 | 4 | 5 |
| A |   | Liquid paraffin | 18 | 27 | 17 | 15 | 15 | 12 | 20 |   | 9 |   |   | 15 | 20 |
|   | A1 | Vaseline | 1 | 1 | 3 | 5 | 5 | 8 | 10 | 10 | 0.5 | 15 | 10 | 5 | 10 |
|   | A2 | Isostearic acid | 1 | 0.5 | 3 | 5 | 3 | 4 | 20 | 20 | 0.5 | 20 | 10 | 5 | 10 |
|   |   | Oleic acid |   |   |   |   | 2 | 4 |   |   |   |   |   |   |   |
|   |   | Oleyl alcohol |   |   | 2 |   |   | 4 |   |   |   |   |   |   |   |
|   |   | Isopropyl myristate |   |   |   |   |   | 3 |   |   |   |   |   |   |   |
|   |   | Isopropyl palmitate |   | 0.5 |   | 5 | 5 |   |   |   |   | 5 |   | 5 | 10 |
| B |   | Concentrated glycerin | 20 | 11 | 15 | 25 | 25 | 35 | 30 | 50 | 10 | 50 | 60 | 25 | 50 |
|   |   | Acrylate-alkyl methacrylate copolymer | 0.2 | 0.3 | 0.2 | 0.2 | 0.2 | 0.2 | 0.2 | 0.2 | 0.2 | 0.2 | 0.2 |   |   |
|   |   | 48% liquid caustic soda | 0.1 | 0.15 | 0.1 | 0.1 | 0.1 | 0.1 | 0.1 | 0.1 | 0.1 | 0.1 | 0.1 |   |   |
|   |   | Polyoxyethylene sorbitan fatty acid ester |   |   |   |   |   |   |   |   |   |   |   | 4 |   |
|   |   | Sorbitan fatty acid ester |   |   |   |   |   |   |   |   |   |   |   | 1 |   |
| C |   | Purified water | 59.7 | 59.55 | 59.7 | 44.7 | 44.7 | 29.7 | 19.7 | 19.7 | 79.7 | 9.7 | 19.7 | 40 | 0 |
|   |   | Total (% by mass) | 100 | 100 | 100 | 1001 | 100 | 100 | 100 | 100 | 100 | 100 | 100 | 100 | 100 |
|   |   | Viscosity (mPa·s) | 4000 | 15000 | 9000 | 12000 | 12000 | 16000 | 19000 | 23000 | 3000 | 26000 | 20000 | 20 | 300 |
| Ratings |   | Ease of application | 5 | 5 | 5 | 5 | 5 | 4.3 | 3.3 | 3.7 | 5 | 2.3 | 3.3 | 4.3 | 1.3 |
|   |   | Moist feeling | 3.7 | 3.7 | 4.7 | 5 | 5 | 5 | 5 | 5 | 2 | 5 | 5 | 2.7 | 3.7 |
|   |   | Non-stickiness | 5 | 5 | 5 | 5 | 5 | 4.3 | 3.7 | 3.3 | 5 | 3.3 | 2 | 4 | 1.3 |

The samples according to Examples 1 to 8 of the present invention had good ratings for all of the ease of application, moist feeling, and non-stickiness. The sample according to Comparative Example 1, which contained little amount of oily ingredients, was inferior in the moist feeling, and the sample according to Comparative Example 2, which contained little amount of water, and the sample according to Comparative Example 3, which contained a large amount of glycerin, were inferior in the ease of application and non-stickiness. Moreover, the sample according to Comparative Example 4, which was emulsified using surfactants in place of a water-soluble polymer, had a poor moist feeling, and was slightly inferior in the ease of application and non-stickiness. In addition, the oil-based body lotion according to Comparative Example 5 was slightly inferior in the moist feeling after application to the wetted skin, and was also poor in the ease of application and non-stickiness.

Furthermore, using the compositions of Example 4 and Comparative Example 4, a change in a moisture content of a stratum corneum after bathing was measured in a method described below. The results are shown in FIG. 1. It can be seen from FIG. 1 that when the composition of the invention is applied to wetted skin and then dried with a towel, the moisture content of the stratum corneum can be retained for a long time. Note that the moisture content of the stratum corneum shown in FIG. 1 is expressed by a differential value between the moisture content before bathing (the value before bathing) and the moisture content after bathing.

<Test Method>

A forearm was washed with a soap and dried with a towel, and acclimated to a testing environment (room temperature: 20° C.; humidity: 40% RH) for 30 minutes, after which a moisture content of a stratum corneum (the value before bathing) was measured. The forearm was subsequently soaked in a bath tub at 40° C. for 10 minutes. After bathing, each composition was applied to the wetted skin (0.2 g to an inner side of the forearm) and dried with a towel, and then the moisture content of the stratum corneum was measured with the passage of time.

The moisture content of the stratum corneum was measured using a Corneometer (manufactured by Integral Corporation) for the skin moisture content.

The invention claimed is:

1. An oil-in-water body cosmetic for application to wetted skin, comprising a water-soluble polymer, and components (A) to (C):
   (A) from 20 to 50% by mass of oily ingredients comprising (A1) oil which is pasty at 25° C. and (A2) polar oil which is liquid at 25° C., said polar oil comprising a fatty acid as an acid with 12 to 28 carbon atoms which is liquid at 25° C.;
   (B) from 11 to 50% by mass of glycerin; and
   (C) from 20 to 60% by mass of water;
   a content of the pasty oil (A1) in the cosmetic being from 1 to 20% by mass, and a content of the liquid polar oil (A2) in the cosmetic being from 3 to 20% by mass, and wherein the body cosmetic contains no surfactant in an amount greater than 0.1%.

2. The body cosmetic according to claim 1, wherein the mass ratio of the ingredient (A1) to the ingredient (A2) is from 1:20 to 10:1.

3. The body cosmetic according to claim 1, wherein the water-soluble polymer is present in the body cosmetic in an amount of from 0.01 to 10% by mass.

4. The body cosmetic according to claim 1, wherein the water-soluble polymer is present in the body cosmetic in an amount of from 0.05 to 5% by mass.

5. The body cosmetic according to claim 1, wherein ingredient (A1) has a melting point of from 30 to 90° C.

6. The body cosmetic according to claim 1, wherein ingredient (A1) is vaseline or paraffin.

7. The body cosmetic according to claim 1, wherein component (A) is present in an amount of from 25 to 35% by mass.

8. The body cosmetic according to claim 1, wherein ingredient (A1) is present in an amount of from 2 to 8% by mass.

9. The body cosmetic according to claim 1, wherein ingredient (A2) is present in an amount of from 5 to 15% by mass.

10. The body cosmetic according to claim 1, wherein the mass ratio of the ingredient (A1) to the ingredient (A2) is from 1:10 to 2:1.

11. The body cosmetic according to claim 1, wherein component (A) comprises oil ingredients in addition to ingredients (A1) and (A2), in an amount of from 1 to 30% by mass.

12. The body cosmetic according to claim 1, wherein component (B) is present in an amount of from 15 to 45% by mass.

13. The body cosmetic according to claim 1, wherein component (B) is present in an amount of from 15 to 35% by mass.

14. The body cosmetic according to claim 1, wherein the total amount of components (A) and (B) is 80% by mass or less.

15. The body cosmetic according to claim 1, wherein the total amount of components (A) and (B) is 30 to 70% by mass.

16. The body cosmetic according to claim 1, wherein component (C) is present in an amount of from 30 to 50% by mass.

* * * * *